US009676695B2

(12) United States Patent
Nunley et al.

(10) Patent No.: US 9,676,695 B2
(45) Date of Patent: Jun. 13, 2017

(54) METHODS FOR INTEGRATED NATURAL GAS PURIFICATION AND PRODUCTS PRODUCED THEREFROM (75) Inventors: Mark Allen Nunley, Charleston, WV (US); Madan Mohan Bhasin, Charleston, WV (US); William George Etzkorn, Hopewell, OH (US); George Ernest Keller, II, South Charleston, WV (US); Parvez H. Wadia, Charleston, WV (US)

(73) Assignee: Aither Chemical LLC

( * ) Notice: Subject to any disclaimer, the term of this patent is extended or adjusted under 35 U.S.C. 154(b) by 0 days.

(21) Appl. No.: 13/408,759

(22) Filed: Feb. 29, 2012

(65) Prior Publication Data
US 2012/0222422 A1   Sep. 6, 2012

Related U.S. Application Data (60) Provisional application No. 61/448,441, filed on Mar. 2, 2011.

(51) Int. Cl.
| C07C 69/00 | (2006.01) |
| C07C 51/215 | (2006.01) |
| C07C 67/055 | (2006.01) |
| C07D 301/03 | (2006.01) |
| C07C 5/333 | (2006.01) |
| E21B 43/34 | (2006.01) |

(52) U.S. Cl.
CPC ............ *C07C 51/215* (2013.01); *C07C 5/333* (2013.01); *C07C 67/055* (2013.01); *C07D 301/03* (2013.01); *E21B 43/34* (2013.01)

(58) Field of Classification Search
CPC ..... C07C 51/215; C07C 5/333; C07C 67/055; C07C 11/04; C07C 53/08; C07C 69/15; C07D 301/03; E21B 43/34
USPC .......... 526/329; 549/518; 560/265; 568/449; 585/510, 606, 638, 654, 733, 734
See application file for complete search history.

(56) References Cited

U.S. PATENT DOCUMENTS

| 4,250,346 A | 2/1981 | Young et al. |
| 4,524,236 A | 6/1985 | McCain |
| 4,568,790 A * | 2/1986 | McCain ................. B01J 23/002 502/311 |
| 4,822,578 A | 4/1989 | Busse et al. |
| 4,899,003 A | 2/1990 | Manyik et al. |
| 5,015,799 A | 5/1991 | Walker et al. |
| 5,155,262 A | 10/1992 | Etzkorn et al. |
| 5,162,578 A | 11/1992 | McCain, Jr. et al. |
| 5,183,936 A | 2/1993 | Etzkorn et al. |
| 5,198,578 A | 3/1993 | Etzkorn et al. |
| 5,639,929 A | 6/1997 | Bharadwaj et al. |
| 5,691,262 A | 11/1997 | Hagemeyer et al. |
| 5,744,547 A * | 4/1998 | Moritani et al. ............. 525/62 |
| 5,759,946 A | 6/1998 | Hoang et al. |
| 5,780,700 A | 7/1998 | Hagemeyer et al. |
| 5,821,384 A | 10/1998 | Zoeller et al. |
| 5,902,918 A | 5/1999 | Hagemeyer et al. |
| 5,905,180 A | 5/1999 | Yokoyama et al. |
| 5,994,420 A * | 11/1999 | Gusavage ................. B32B 5/18 521/146 |
| 6,040,474 A | 3/2000 | Jobson |
| 6,072,097 A | 6/2000 | Yokoyama et al. |
| 6,130,183 A | 10/2000 | Herskowitz et al. |
| 6,235,678 B1 | 5/2001 | Mamedov et al. |
| 6,239,325 B1 | 5/2001 | Kishimoto et al. |
| 6,248,794 B1 | 6/2001 | Gieskes |
| 6,355,854 B1 | 3/2002 | Liu |

(Continued)

FOREIGN PATENT DOCUMENTS

| CA | 2204677 A1 * | 5/1997 |
| CA | 2204677 * | 11/1997 |

(Continued)

OTHER PUBLICATIONS

Valenzuela et al. (Nanostructured ceria-based catalysts for oxydehydrogenation of ethane with CO2 Topics in Catalysis vol. 15, No. 2-4, 2001).*
Valenzuela et al. (Nanostructured ceria-based catalysts for oxydehydrogenation of ethane with CO2 Topics in Catalysis vol. 15, No. 2-4, 2001.*
Weitkamp et al. (Products of the Hydrogenation of Carbon Monoxide over an Iron Catalyst, Industrial and Engineering Chemistry vol. 45, No. 2, 1953).*
Ping et al. (Actnation of Ethane in Wet Natural Gas Over a Mn2O3/SiO2 Catalyst, Journal of Natural gas Chemistry, vol. 8 No. 1, 1999).*

(Continued)

*Primary Examiner* — Yevegeny Valenrod
*Assistant Examiner* — Blaine G Doletski
(74) *Attorney, Agent, or Firm* — Dinsmore & Shohl, LLP; Monika L. Jaensson, Esq.

(57) ABSTRACT

A method is disclosed of coupling and integrating natural gas recovery and separation along with chemical conversion. The method can comprise extracting at least one natural gas component. Non-limiting examples of the extracted component include ethane, propane, butanes, and pentanes. The method can also comprise contacting a natural gas stream with a catalyst under conditions that selectively convert at least one component into at least one product, such as ethylene, acetic acid, polyethylene, vinyl acetate, ethylene vinyl acetate, ethylene oxide, ethylene glycol, and their derivatives, propylene, polypropylene, propylene oxide, propylene glycol, acrylates, acrolein, acrylic acid, butenes, butadiene, methacrolein, methacrylic acid, methacrylates, and their derivatives, which can then be separated from the remaining components. The method can further comprise integrating production of ethylene, acetic acid, and/or vinyl acetate with polymerization of ethylene-based polymers, such as polyethylene, ethylene vinyl acetate, ethylene vinyl alcohol, polyvinyl acetate, or polyvinyl alcohol.

29 Claims, 3 Drawing Sheets

(56) References Cited

U.S. PATENT DOCUMENTS

| | | | |
|---|---|---|---|
| 6,403,523 B1 | 6/2002 | Cantrell et al. | |
| 6,436,871 B1 | 8/2002 | Liu | |
| 6,452,061 B1 | 9/2002 | Schmidt et al. | |
| 6,518,476 B1 * | 2/2003 | Culp | C07C 2/84 585/655 |
| 6,521,808 B1 | 2/2003 | Ozkan et al. | |
| 6,531,638 B2 | 3/2003 | Ingallina et al. | |
| 6,541,418 B1 | 4/2003 | Al-Zahrani et al. | |
| 6,548,447 B1 | 4/2003 | Yokoyama et al. | |
| 6,576,803 B2 | 6/2003 | Cantrell et al. | |
| 6,586,360 B1 | 7/2003 | Ingallina et al. | |
| 6,605,739 B1 | 8/2003 | Karim et al. | |
| 6,635,794 B2 | 10/2003 | Kishimoto | |
| 6,743,829 B2 | 6/2004 | Fischer-Calderon et al. | |
| 6,756,517 B2 | 6/2004 | Kishimoto et al. | |
| 6,790,983 B1 | 9/2004 | Zeyss | |
| 6,831,204 B2 | 12/2004 | Chen et al. | |
| 6,846,773 B1 | 1/2005 | Yokoyama et al. | |
| 6,852,877 B1 | 2/2005 | Zeyss et al. | |
| 6,858,768 B2 | 2/2005 | Budin et al. | |
| 7,067,455 B2 | 6/2006 | Chen et al. | |
| 7,211,688 B2 | 5/2007 | Clarke | |
| 7,227,049 B2 | 6/2007 | Liu | |
| 7,256,319 B2 | 8/2007 | Al-Zahrani et al. | |
| 7,319,179 B2 | 1/2008 | López Nieto et al. | |
| 7,390,918 B2 | 6/2008 | Clarke et al. | |
| 7,402,719 B2 | 7/2008 | Brophy et al. | |
| 7,411,107 B2 | 8/2008 | Lucy | |
| 7,491,843 B2 | 2/2009 | Jobson et al. | |
| 7,744,829 B2 | 6/2010 | Brophy et al. | |
| 7,767,770 B2 | 8/2010 | Han et al. | |
| 2004/0158112 A1 * | 8/2004 | Ramani | B01J 23/626 585/658 |
| 2008/0132723 A1 * | 6/2008 | Johnston | C07C 5/48 560/241 |
| 2009/0156870 A1 | 6/2009 | Lauritzen et al. | |
| 2009/0292139 A1 * | 11/2009 | Brazdil et al. | 562/512.2 |
| 2009/0318743 A1 * | 12/2009 | Arnold et al. | 585/658 |
| 2010/0168466 A1 | 7/2010 | Johnston et al. | |
| 2010/0222623 A1 | 9/2010 | Ryan | |
| 2010/0331587 A1 | 12/2010 | Petitjean | |

FOREIGN PATENT DOCUMENTS

| | | | |
|---|---|---|---|
| WO | WO 98 05620 | * | 2/1998 |
| WO | WO 2008 075031 A1 | * | 6/2008 |

OTHER PUBLICATIONS

AU25 (AU602025, 1990, all references to AU25 are made to a machine translation).*

Natural Gas Processing "NGP" (Natural Gas Processing: The Crucial Link Between Natural Gas Production and its Transportation to Market 2006).*

Manely, (Thermodynamically Efficient Distillation: Ethylene Recovery, Department of Chemical Engineering, University of Missouri—Rolla, 2009).*

Greddes (Polyvinyl and Ethylene-Vinyl Acetates, in Handbook of Adhesive Technology, Pizzi et al., Eds., at Chapter 35, CRC Press, 2003).*

Celanese (2009).*

Lillies et al. (Sand Fracturing with Liquid Carbon Dioxide, society of Petroleum Engineers, 1982).*

Of Natural Gas Processing "NGP" (Natural Gas Processing: The Crucial Link Between Natural Gas Production and its Transportation to Market, 2006).*

Triebe et al. (Adsorption of methane, ethane and ethylene on molecular sieve zeolites, Gas. Sep. Purif. vol. 10, No. 1, pp. 81-84, 1996).*

Geddes, Handbook of Adhesive Technology, Chptr. 35, 2003, CRC Press.

Geddes, K. (2003) "Polyvinyl and Ethylene—Vinyl Acetates." In *Handbook of Adhesive Technology*, Pizzi et al., Eds., at Chapter 35, CRC Press.

Foss, Michelle Michot "Interstate Natural Gas—Quality Specifications & Interchangeability" Center for Energy Economics, Dec. 2004, 52 pages [online]. Retrieved from the Internet: http://www.beg.utexas.edu/energyecon/lng/documents/CEE_Interstate_Natural_Gas_Quality_Specifications_and_Interchangeability.pdf.

International Search Report and Written Opinion issued in International Patent Application No. PCT/US2012/027103, mailed Aug. 16, 2012.

* cited by examiner

METHODS FOR INTEGRATED NATURAL GAS PURIFICATION AND PRODUCTS PRODUCED THEREFROM

This application claims the benefit of U.S. Provisional Patent Application Ser. No. 61/448,441, filed on Mar. 2, 2011, which is herein incorporated in its entirety.

TECHNICAL FIELD

The present invention is generally directed toward natural gas processing and, more specifically, toward novel process coupling and integration for natural gas recovery and separation along with chemical conversion to provide a relatively purified natural gas stream and further to produce higher value products.

BACKGROUND

Natural gas consists primarily of methane, approximately greater than ninety mole percent (>90 mol %). Raw natural gas extracted from a well commonly exists in mixtures with other hydrocarbons, principally ethane, propane, butanes, and pentanes. In addition, raw natural gas contains water vapor, hydrogen sulfide ($H_2S$), carbon dioxide, helium, nitrogen, and small quantities of other compounds.

Natural gas processing involves separating all of the various hydrocarbons and fluids from the raw natural gas, which is primarily methane, to produce what is known as "pipeline quality" dry natural gas. The owners of major interstate transportation pipelines, as well as local distribution companies, usually impose restrictions on the make-up of the natural gas that is allowed into the pipeline. Therefore, natural gas is typically purified before it is transported from its origin to remove, e.g., to remove water, hydrogen sulfide, and carbon dioxide. As a term of art in the natural gas industry, "pipeline quality" gas has come to mean natural gas that (1) has a heating value within five percent (+/−5%) of the heating value of pure methane, or 1,010 Btu per cubic foot under standard atmospheric conditions, and (2) is free of water and toxic or corrosive contaminants. See *The Natural Gas Industry: Evolution, Structure, and Economics*, Arlon R. Tussing and Bob Tippe, Pennwell Books, 1995. However, each pipeline operator individually determines the applicable quality specifications based on the particular supply sources, operational constraints, and end user requirements. See *Interstate Natural Gas—Quality Specifications & Interchangeability*, Michelle Michot Foss, Center for Energy Economics, Institute for Energy, Law & Enterprise, University of Houston Law Center (December 2004) available at http://www.beg.utexas.edu/energyecon/lng/documents/CEE_Interstate_Natural_Gas_Quality_Specifications_and_Interchangeability.pdf. There is not a single specification that applies to all natural gas pipelines, although most pipelines have similar quality requirements and all must meet certain baseline requirements to ensure safe pipeline operation and comply with government regulations. Therefore, as used herein, "pipeline quality" natural gas means gas that meets the general range of gas specifications giving rise to this requirement within the U.S. gas transportation industry.

While certain amounts of the ethane, propane, butanes, and pentanes typically are removed from natural gas, this does not mean that they are all "waste products." In fact, those associated hydrocarbons are typically very valuable by-products of natural gas processing and can be sold separately. Those hydrocarbons have a variety of different uses, including enhancing oil recovery in oil wells, providing raw materials for oil refineries or petrochemical plants, and as sources of energy. For example, the liquefied petroleum gas ("LPG") used in home heating, cooking, and transportation engines is a combination of propane and butanes obtained from natural gas processing. However, the actual practice of processing natural gas to pipeline dry gas quality levels is quite complex and energy intensive.

Natural gas streams require a number of pre-processing and processing steps before the components, e.g., dry natural gas and Natural Gas Liquids ("NGL"), attain specifications that permit their transport and sale as commercially viable products. Large classes of natural gas wells can generate processed gas streams in which the ethane content is too high to recover optimal value of the dry natural gas product, yet too low to justify economically its removal from the natural gas product. In some of these cases, NGL pipelines can safely and effectively transport the heavier hydrocarbons (e.g., propane and butanes), but cannot safely transport gaseous ethane streams. In these cases the ethane becomes stranded at the gas processing or well-source location. With limited or no attractive economical purification, transport, or use options, the only viable option is to burn the natural gas stream for fuel value. A process that can remove the problems presented by stranded ethane gas within natural gas source areas will provide economic and potential environmental advantages.

Additionally, one option for natural gas processing is to convert certain constituents obtained from natural gas into olefins, which have a variety of uses. This is typically accomplished by the non-catalytic thermal or steam cracking of saturated hydrocarbons, such as ethane and/or propane and/or butanes, or the catalytic dehydrogenation of ethane and/or propane and/or butanes. A typical ethylene plant using steam cracking of ethane achieves an ethylene selectivity up to about 80-85% calculated on a carbon atom basis at a per pass ethane conversion of about 65-60%, respectively. But steam or thermal cracking processes, as well as catalytic dehydrogenation processes, for olefin production are highly endothermic. Therefore, these processes consume a large amount of energy and require large, capital-intensive, and complex cracking furnaces to supply the requisite heat. Steam or thermal cracking processes also typically produce a large number of by-products, including propylene, butenes, higher olefins, diolefins, benzene, toluene, xylenes, and acetylenes, as well as higher alkanes and other higher hydrocarbons. Therefore, cracking processes require extensive refining to separate the by-products into useful components for sale or manufacture of other products. Currently, over 90% of the ethylene produced in the world is derived from naphtha steam cracking, with the balance of about 10% being from ethane, propane, and butane steam cracking.

Naphtha steam cracking is a highly endothermic process, requiring large energy input and large, capital-intensive, and complex cracking furnaces. Naptha steam cracking also produces a variety of products other than ethylene, including propylene, propane, butenes, butanes, higher olefins, diolefins, benzene, toluene, xylenes, and acetylenes. These byproducts are costly to separate from ethylene, which is usually done by cryogenic distillation, extractive distillation, and/or selective hydrogenation to the corresponding mono-olefin, e.g. acetylene to ethylene.

Steam cracking facilities, with the supporting infrastructures and processes, are among the most complex projects in the petrochemical industry, requiring a tremendous initial investment to construct a plant on an economically viable scale. Additionally, upstream refining, separation, and purification processes, e.g., distillation or adsorption, are typically capital and energy intensive processes. Storing and transporting high purity hydrocarbon feedstock, particularly gases like ethane, presents substantial environmental and safety risks, requiring further capital and energy intensive processes. In order to make a steam cracking process capital efficient, it is typically conducted on an extremely large scale, e.g., a typical plant may produce about 2 billion pounds of ethylene per year.

There are existing processes that utilize purified hydrocarbon feedstock, particularly ethane, derived from natural gas. Those processes typically require a high purity feedstock (e.g., approximately greater than ninety-nine percent (>99%)) that involves upstream refining, separation, purification, and supply infrastructure. The processes for converting a high purity, natural gas-derived hydrocarbon feedstock, particularly ethane, to a more valuable commodity chemical, particularly ethylene, acetic acid, ethylene oxide, and/or vinyl acetate monomer ("VAM"), do not facilitate or incorporate value from the back-integrated use of impure hydrocarbon feed streams, such as ethane derived from the processing of natural gas. Some processes have been described for some limited integrated production of ethylene, acetic acid, and VAM from high purity ethylene, but those processes similarly do not facilitate or incorporate value from the back-integrated use of impure ethane feed streams. In addition, even the limited integration described does not fully utilize all of the possible forward or downstream process integration.

For example, U.S. Pat. Nos. 4,250,346; 4,524,236; 4,899,003; and 5,162,578, which are incorporated herein by reference, disclose ethane oxydehydrogenation ("EODH") processes whereby ethane and an oxidant, typically oxygen or air, is converted into ethylene and/or acetic acid. EODH is an exothermic process and, therefore, requires diluents to control the heat produced during the reaction. Typically, the best diluents are those gases with a high heat capacity. For example, U.S. Pat. Nos. 5,155,262; 5,183,936; and 5,198,578, which are incorporated herein by reference, demonstrate the effects of diluent heat capacity on the performance of catalytic oxidation processes, particularly the conversion of propylene and isobutylene to acrolein and methacrolein, respectively.

The existing EODH processes are also not able to take full advantage of the exothermic nature of the EODH process, because they do not allow for downstream integration. Some of those processes are exclusively focused on producing ethylene from ethane and, thus, do not enable the benefits of integration with downstream and upstream processes, which can benefit from the heat generation. Similarly, those processes that lack downstream integration do not benefit from the advantageous generation of acetic acid as a by-product of the EODH process. Likewise, some processes focus on producing acetic acid from ethane and, thus, do not enable the benefits of integration with upstream and downstream processes, such as those that benefit from the advantageous generation of ethylene. Some of those processes enable the co-production of ethylene and acetic acid from ethane, but they do not enable the benefit of back-integration for upstream use of methane and other high heat capacity diluents from impure ethane-containing natural gas streams.

EODH is only one type of a catalytic oxydehydrogenation ("ODH") process that is specifically applied to ethane, but other alkanes can also be converted to alkenes and alkene derivatives by ODH processes. For example, U.S. Pat. Nos. 5,639,929; 5,780,700; 5,902,918; 6,072,097; 6,235,678; 6,355,854; 6,576,803; 6,756,517; 6,846,773; 6,858,768; and 7,067,455, which are incorporated herein by reference, disclose ODH processes for converting hydrocarbons into olefins. Those processes suffer from the same deficiencies as the previously described EODH processes, specifically they require feedstocks that have been previously purified to remove the non-reactant alkanes and other impurities. Therefore, the previously described processes do not enable backward (or upstream) integration with raw natural gas streams and they are not integrated with forward or downstream processes.

Vinyl acetate monomer (VAM) is manufactured from the oxidative reaction of ethylene and acetic acid. U.S. Pat. No. 5,821,384 and the like describe processes for converting ethylene and acetic acid in the presence of an oxidant and a catalyst into VAM. Furthermore, U.S. Pat. Nos. 6,040,474; 6,605,739; 6,040,474; and 7,491,843 describe processes for the integration of an EODH process for manufacturing ethylene and acetic acid with a downstream process for manufacturing VAM. However, those processes do not enable the benefits of integration of further downstream and upstream processes, particularly utilization of impure natural gas feedstocks and further derivatization or polymerization of VAM. In addition, those processes do not integrate the removal of carbon oxides and their subsequent utilization in further downstream processes.

Ethylene and vinyl acetate may be copolymerized to prepare a range of useful products that vary in properties and performance, depending on the ratio of ethylene to vinyl acetate in the polymer. Ethylene vinyl acetate ("EVAc") copolymer is manufactured by the free radical polymerization of VAM and ethylene at high pressure and temperatures. As used herein, EVAc is meant to represent any and all copolymers of ethylene and vinyl acetate, regardless of the ethylene-vinyl acetate ratio. Previously described processes for producing EVAc and its copolymers do not include the integration of ethane-containing feedstocks (e.g., unpurified natural gas), ethylene production, VAM production, or the ability to derive these products alone from ethane-containing feedstocks. In addition, those processes do not include the ability to integrate with upstream processes for producing ethylene, VAM, and/or acetic acid, such as the EODH process. Particularly useful integration steps disclosed herein include, without limitation, carbon dioxide utilization, heat and energy utilization, and compression.

There is a need for a process that enables the use of ethane to capture higher value products while integrating by-product utilization and energy recovery to provide lower cost and reduced environmental impact.

SUMMARY OF CERTAIN EMBODIMENTS

The present invention satisfies the needs discussed above as it is generally directed toward natural gas processing and, more specifically, toward novel process coupling and integration for natural gas recovery and separation along with chemical conversion to provide a relatively purified natural gas stream and further to produce higher value products.

In order to address the high costs and inefficiencies associated with large scale natural gas processing systems, the present invention seeks to implement a more flexible and efficient processing system, involving the integration of natural gas purification and production of higher value hydrocarbon-based products. The present invention provides for a process that can also be implemented at a relatively smaller scale with fewer select products, fewer by-products, and lower cost. The integrated chemical conversion processes of the present invention allow for the recovery of a predominantly methane product natural gas stream, which may be "pipeline quality" dry natural gas or could be mixed with other natural gas sources, e.g. natural gas that is rich in $C_2$+ hydrocarbons, to make the resulting mixture "pipeline quality" dry natural gas.

In one embodiment, the present invention enables the direct utilization of natural gas streams, including raw or minimally purified natural gas streams, in the production of higher value hydrocarbon-based products, particularly ethane-based products. Higher value hydrocarbon-based products typically are produced from ethylene, propylene, and other olefins that are traditionally obtained from steam crackers. For example, the present invention enables the flexible utilization of ethane through the downstream and/or backward integration of processes for producing ethylene and/or acetic acid with processes that consume those products in the production of vinyl acetate ("VAM"), ethylene-vinyl acetate copolymers ("EVAc"), ethylene-vinyl alcohol copolymers ("EVA"), polyvinyl alcohol ("PVA"), and/or polyvinyl acetate ("PVAc"). Further integration enables production of polyethylene ("PE"), ethylene oxide ("EO"), other ethylene derivatives, acetic acid, and/or their derivatives.

One aspect of the present invention includes a process for removing at least one hydrocarbon component(s) from a natural gas stream. This component can include ethane, propane, butanes, and/or pentanes. The component may be substantially completely removed from the subject natural gas stream or only a fraction of the component may be removed from the natural gas stream. Accordingly, in one embodiment, the present invention enables a process involving removing some fraction of ethane or other hydrocarbons from a natural gas stream, converting the ethane or other hydrocarbons into higher value products, recovering those products, and returning the unconverted ethane or other hydrocarbons to the natural gas stream for further recovery, processing, and/or distribution and sale.

For example, ethane can be removed from a natural gas stream by converting the ethane to acetic acid, ethylene, ethylene derivatives such as ethylene oxide, acetic acid derivatives, and/or other derivatives. In addition, methane can be removed by converting it to ethane, which can then be converted to acetic acid, ethylene, ethylene derivatives such as ethylene oxide, acetic acid derivatives, and/or other derivatives. If propane is removed from a natural gas stream, it can be removed by converting it to propylene, acrolein, acrylic acid, acrylates, polypropylene, propylene oxide, propylene glycol and/or other derivatives. When butanes are removed, they can be removed by converting the butanes, which typically refers to a mixture of n-butane and isobutane, to butenes, butadiene, methacrolein, methacrylic acid, methacrylates, and/or other derivatives.

This aspect of the present invention can also include the creation of a substantially methane-rich stream, which is recovered as a product from a natural gas stream after removal of ethane, propane, butanes, and/or pentanes by a combination of chemical conversion as well as conventional separation techniques. In another aspect of the present invention, this substantially methane-rich stream can also be subjected to reactive conversion processes, e.g., oxidation, oxidative coupling, or gas-to-liquids processes, integrated with other processes according to aspects of the present invention. Integrated methane reactive conversion processes produce methane-derived products, e.g., methanol or formaldehyde that can be further utilized in integrated processes or separated and sold. Further, ethylene, acetic acid, vinyl acetate monomer, and ethylene-vinyl acetate copolymers can be additional products of the process.

Still another aspect of the present invention involves removing all or a portion of the ethane contained in a natural gas stream by an EODH process, with subsequent recovery of products. The ethane can be converted to ethylene, acetic acid, and/or VAM. The ethylene and the acetic acid can be produced in a ratio such that they are substantially consumed during the production of VAM followed by recovery of the vinyl acetate monomer, which can then be recovered or further utilized in the integrated process of the present invention. Alternatively or additionally, the ethylene and vinyl acetate monomer can be produced in a ratio such that they are substantially consumed during ethylene-vinyl acetate copolymers, which can then be recovered or further utilized in the integrated process of the present invention. Further, the water and carbon dioxide by-products of the EODH process can be used at least in part in an ethane conversion process. The carbon dioxide can also be used to aid in the refining ethylene, VAM, and various polymers and foams, including EVA and EVAc. Further, the carbon dioxide can be recovered for sale.

Further, another aspect of the present invention involves the production of polymers such as PVA, PVAc, EVAc, EVA, and/or ethylene in a process that is integrated with the production of ethylene and acetic acid from ethane. One aspect of the present invention is the production of those polymers from an ethane-containing stream. The ethane-containing stream may be an unpurified natural gas stream, an ethane-enriched natural gas stream, or a substantially pure ethane gas stream. The invention further enables the integrated utilization of water and/or acetic acid by-products to stop the polymerization reaction in the preparation of PVA, PVAc, EVA, or EVAc. In addition, the invention enables the utilization of excess heat and energy produced in the exothermic polymerization reaction in endothermic aspects of an integrated process according to the invention. Likewise, the invention enables the integrated utilization of compression throughout the process from the natural gas supply through the downstream processes for producing polymers.

The foregoing and other features of the present disclosure will be more readily apparent from the following detailed description of exemplary embodiments, taken in conjunction with the attached drawings. It will be noted that, for convenience, many of the illustrations of devices herein show the height dimension exaggerated in relation to the width.

It is to be understood that the present disclosure and the various embodiments of the described invention is not limited in its application to the details of the construction and arrangement of parts illustrated in the accompanying drawings. The invention is capable of other embodiments and of being practiced or carried out in a variety of ways. It is to be understood that the phraseology and terminology employed herein are for the purpose of description and not of limitation.

DETAILED DESCRIPTION OF CERTAIN EMBODIMENTS

Definitions

The term, "selectively extracting" or "selective extraction" means removing a component of a gas stream and leaving the remainder of the gas stream unaffected. The means of effecting this "selective extraction" may be any of the standard separation techniques in practice in the field of chemical engineering, including, for example, distillation, absorption, adsorption, metal-complexation, condensation, extraction, scrubbing, stripping, and the use of membranes. "Selective extraction" also includes novel separation techniques, such as those disclosed herein, involving selectively converting particular components from the full gas stream into one or more products of the components.

The term, "selectively converting" or "selective conversion" means performing a chemical reaction on a gas stream in which one or more selected components of the gas stream are converted into one or more products of the components, and leaving the remainder of the gas stream unaffected.

The term, "substantially consumed" means that less than or equal to about fifty percent (50%) of the reactants in a chemical reaction remain in the crude product stream after the reaction is conducted.

The term, "reactive conversion" means a process whereby components of a gas stream are selectively extracted from the gas stream by selective conversion, as defined herein. Exemplary reactive conversion processes include catalytic dehydrogenation, oxidation, and oxydehydrogenation.

The term, "refining" means a process of purifying a natural gas stream to remove impurities and other undesired components, e.g., water vapor, $H_2S$, carbon dioxide, helium, nitrogen, and other compounds.

The term, "pipeline quality" means natural gas that meets the typical industry requirements for introduction into a major natural gas pipeline. Typically, "pipeline quality" dry natural gas (1) has a heating value within five percent (+/−5%) of the heating value of pure methane, or 1,010 Btu per cubic foot under standard atmospheric conditions, and (2) is free of water and toxic or corrosive contaminants.

The term, "higher value products" or "higher value hydrocarbon products" means derivatives of a feedstock, particularly a hydrocarbon feedstock, that have a higher economic value than the feedstock.

The term, "downstream integration" means the integration of processes that utilize a product derived from a reference process with the reference process, e.g., the integration of processes that utilize ethylene derived from an EODH process with the EODH process, wherein EODH is the "reference process." As used herein, "downstream integration" and "forward integration" are synonymous.

The term, "back integration" means the integration of processes that lead to the production of a product by a reference process with the reference process, e.g., the integration of processes that produce ethane for use in an EODH process with the EODH process, wherein EODH is the "reference process." As used herein, "back integration," "backward integration," and "upstream integration" are synonymous.

The term, "NGL" means natural gas liquids, and generally refers to the $C_2$ and higher-carbon hydrocarbon components of natural gas (primarily ethane, propane, butane, isobutane, and pentane). Natural gas is comprised predominantly of methane once the NGL have been removed.

The term, "LNG" means liquefied natural gas, and generally refers to the methane gas with some contained ethane, compressed at moderate pressures.

The term, "LPG" means liquid petroleum gas, and generally refers to the propane and butane components of natural gas, which are employed in the heating-fuel markets.

The term, "gas-to-liquids process," also known as "GTL," means a process for converting gaseous hydrocarbons, e.g., methane, into liquid hydrocarbons, e.g., liquid transportation fuels, such as diesel, kerosene, aircraft fuel, gasoline, or petrol.

Reference will now be made in detail to the present embodiments (exemplary embodiments) of the invention, examples of which are illustrated in the accompanying drawings. Wherever possible, the same reference numbers will be used throughout the drawings to refer to the same or like parts.

Figure 1:
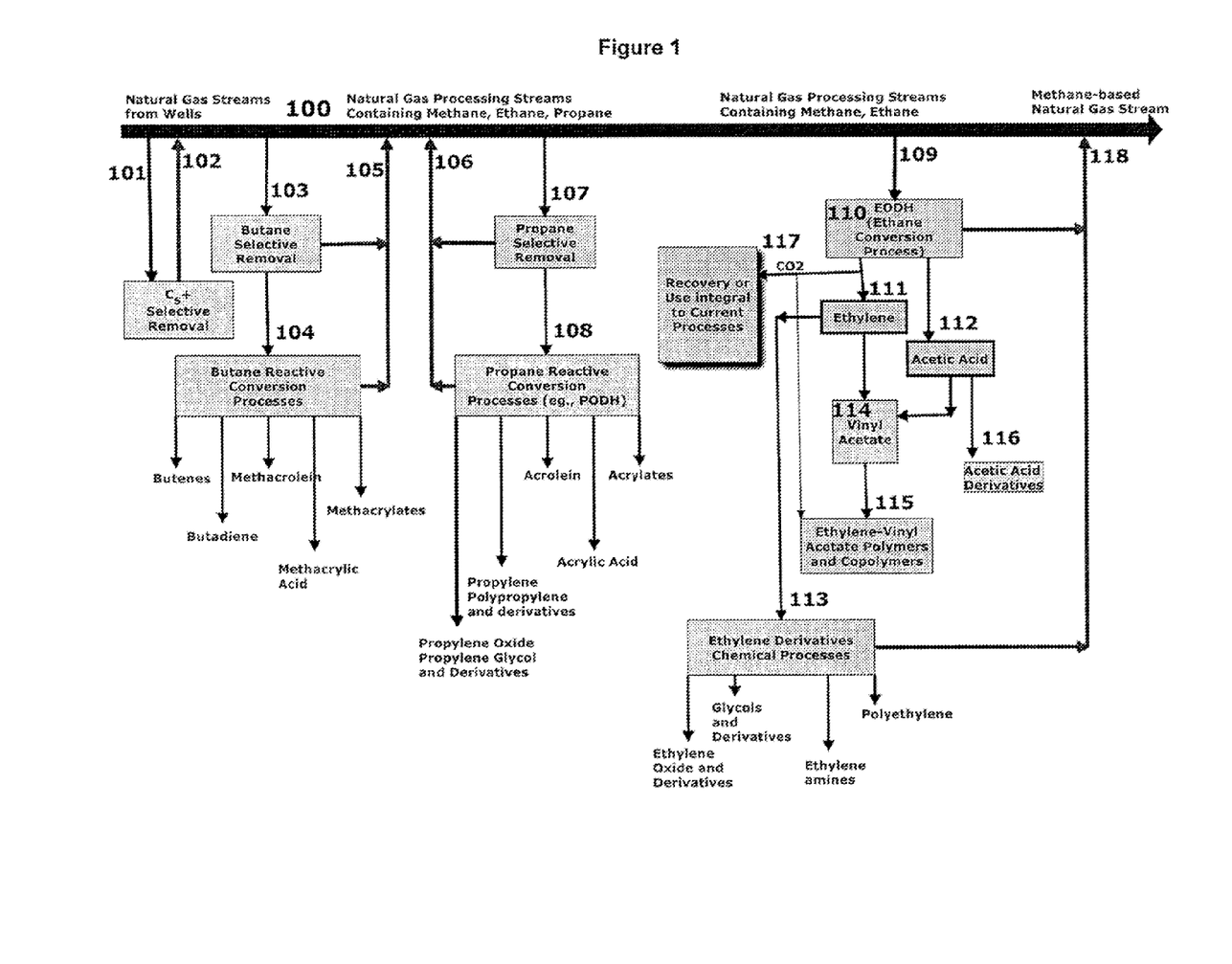
FIG. 1 is a process flow diagram generally demonstrating the integrated removal of components of a natural gas stream and further conversion and/or utilization of the respective components according to one aspect of the present invention.

As illustrated in FIG. 1, natural gas streams recovered from well-sites or from pipelines (100) can be used directly, or with minimal pre-purification, to produce a variety of chemicals according to the integrated approach of the present invention. FIG. 1 exemplifies various aspects of the present invention by illustrating the integration that present invention makes possible. According to one aspect of the present invention depicted in FIG. 1, all or a portion of 100 (i.e., 101) can be subjected to a process in which pentanes and other relatively minor $C_5+$ hydrocarbons are removed from 101 and the resultant natural gas stream, which has a substantially reduced concentration of pentanes and other $C_5+$ hydrocarbons, (102) can be recovered and combined with 100. For example, the natural gas stream 101 can be subjected to a reactive process (e.g., a catalytic reaction with an oxygen source in the presence of an ODH catalyst) that converts pentanes into pentenes and/or their derivatives, which can be separated from the resultant stream 102. Alternatively and/or additionally, 101 may be subjected to a cryogenic distillation and/or adsorption process as a means of separating $C_5+$ hydrocarbons and/or the products of any reaction process from the lighter natural gas fractions (i.e., $<C_5$). The resultant natural gas stream 102 can then be further subjected to processes according to the present invention and/or returned to the gas processing pipelines, streams, or infrastructure (100).

According to another aspect of the present invention, all or a portion of 100 (i.e., 103) can be subjected to an integrated process for selectively removing butanes from the natural gas stream. For example, butanes can be selectively removed from 103 by subjecting it to a conventional separation process such as cryogenic distillation and/or adsorption, with the resultant natural gas stream (105) being further subjected to processes according to the present invention and/or combined with any remaining portion of 100. 105 has a substantially reduced concentration of butanes, and may be substantially free of butanes. The resultant butanes stream (104) can be subjected to a butane reactive conversion process (e.g., a catalytic reaction with an oxygen source in the presence of an ODH catalyst), whereby 104 can be converted into butenes, butadiene, methacrolein, methacrylic acid, and/or methacrylates. The resultant low-butane gas stream (105) can then be further subjected to processes according to the present invention and/or returned to the gas processing pipelines, streams, or infrastructure (100).

In yet another aspect of the present invention, all or a portion of 100 (i.e., 107) can be subject to an integrated process for selectively removing propane from the natural gas stream. For example, propane can be selectively removed from 107 by subjecting it to a cryogenic distillation and/or adsorption process, with the resultant natural gas stream (106) being further subjected to processes according to the present invention and/or combined with any remaining portion of 100. 106 has a substantially reduced concentration of propane, and may be substantially free of propane. The resultant propane stream (108) can be subjected to a propane reactive conversion process (e.g., a catalytic reaction with an oxygen source in the presence of an ODH catalyst), whereby 108 can be converted into propylene, acrolein, acrylates, acrylic acid, propylene oxide, polypropylene, propylene glycol, and other $C_3$-derived compounds. The resultant low-propane gas stream (106) can then be further subjected to processes according to the present invention and/or returned to the gas processing pipelines, streams, or infrastructure (100).

In yet another aspect of the present invention, all or a portion of 100 (i.e., 109) can be subject to an integrated process for selectively removing ethane from the natural gas stream. For example, 109 can be subjected to an EODH process (110) whereby the ethane in 109 is combined with an oxidant, e.g., oxygen or air, and converted into ethylene or acetic acid and steam. The resultant natural gas stream (118) can then be combined with any remaining portion of 100. If propane, butanes, and other heavier hydrocarbons and any impurities have been substantially removed from 118, e.g., according to aspects of the present invention described above, 118 may be considered "pipeline quality" dry natural gas. The by-products of the EODH process, particularly carbon dioxide, carbon monoxide, and water, can be recovered for use in other processes of the present invention.

A variety of process conditions can be employed in the foregoing aspects of the present invention. Those skilled in the art of the present invention can select the appropriate conditions to employ in a particular process. Typically, the foregoing processes are operated at a temperature in the range of about 250 to 500° C., such as about 250 to 400° C., or even about 250 to 350° C., and a pressure in the range of about 1 to 40 atm, such as about 1 to 25 atm, or even about 3 to 15 atm. Exemplary operating conditions are provided in U.S. Pat. Nos. 4,250,346; 4,524,236; 4,899,003; 5,162,578; 5,639,929; 5,780,700; 5,902,918; 6,072,097; 6,235,678; 6,355,854; 6,576,803; 6,756,517; 6,846,773; 6,858,768; and 7,067,455, which are incorporated herein by reference. Particularly useful conditions are provided in U.S. Pat. Nos. 4,250,346 and 4,899,003.

Depending on the conditions employed in the EODH process, e.g., reaction temperature, total pressure, gas hourly space velocity, and the steam partial pressure, the process can be adjusted to favor the production of ethylene (111) or acetic acid (112), or a particular blend of ethylene and acetic acid. All or a portion of the 111 and 112 streams can then be combined in a reactor that produces VAM (114). All or a portion of the resultant VAM can then be converted to PVAc or EVAc, if combined with ethylene, in a polymerization process (115). All or a portion of the recovered carbon dioxide from the EODH process (117) can be used as a blowing agent in the PVAc or EVAc polymerization processes. Carbon dioxide may also be recovered from other processes integrated with EODH, such as oxidation reactions of ethylene to ethylene oxide or propylene to acrylic acid and further purified as a combined stream. Alternatively or additionally, all or a portion of acetic acid stream 112 can be used to produce acetic acid derivatives (116). Further, alternatively or additionally, all or a portion of the ethylene from L can be subjected to further chemical processes (113) to produce ethylene oxide and/or its derivatives, ethylene glycol and/or its derivatives, ethylene amines, and/or polyethylene. The resultant natural gas stream (118) can then be combined with any remaining portion of 100. If propane, butanes, and other heavier hydrocarbons and any impurities have been substantially removed from 118, e.g., according to aspects of the present invention described above, 118 may be considered "pipeline quality" dry natural gas. In another aspect of the present invention, this substantially methane-rich stream can also be subjected to reactive conversion processes, e.g., oxidation, oxidative coupling, or gas-to-liquids processes, integrated with other processes according to aspects of the present invention. Integrated methane reactive conversion processes produce methane-derived products, e.g., methanol or formaldehyde, that can be further utilized in integrated processes or separated and sold.

Another advantageous aspect of the integrated process depicted in FIG. 1 is the ability to improve energy efficiency by redistribution of heat within the overall integrated process. In particular, the ODH processes, e.g., EODH, are exothermic and the excess heat generated by those processes can have multiple uses in the overall integrated process. In one aspect of the integrated process, such excess heat is applied to generate steam, which may be combined with steam produced as a EODH reaction by-product, and subsequently used to generate electricity. In another aspect of the integrated process, such excess heat is utilized to provide energy to an endothermic process, e.g., distillation or a reactive process.

Figure 2:
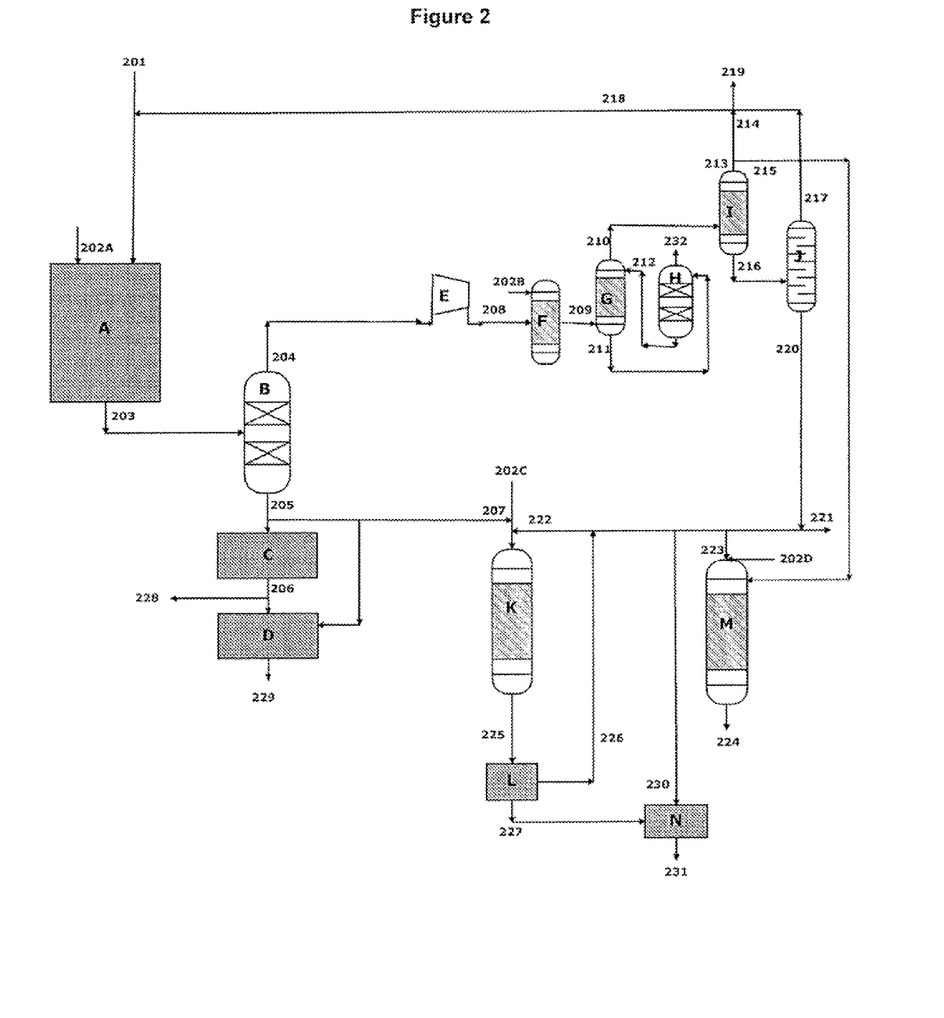
FIG. 2 is a process flow diagram showing an embodiment according to one aspect of the present invention in which ethane is removed from a natural gas stream by converting it into ethylene, acetic acid, VAM, ethylene oxide, and other ethylene derivatives.

An additional embodiment of the present invention is illustrated in FIG. 2. FIG. 2 depicts an integrated process for the conversion of ethane into higher-value chemical products, particularly ethylene, acetic acid, VAM, ethylene oxide, and their derivatives and polymers, from an ethane-containing natural gas stream (201). Table 1 summarizes the process steps shown in FIG. 2. In this integrated process, 201 is combined with an oxidant, e.g., oxygen or air, (202A) and subjected to an EODH process in the presence of an EODH catalyst (A), which produces a product stream comprising ethylene and acetic acid (203). The product stream from A (i.e., 203), which contains ethylene and acetic acid is then separated in a suitable process separation facility (B) to produce an ethylene-containing stream (204) and a stream consisting substantially of acetic acid (205).

TABLE 1

| Process | Description |
|---------|-------------|
| A | EODH Catalytic Reaction System |
| B | Scrubber |
| C | Acetic Acid Refining |
| D | Acetic Acid Derivatives |
| E | Compressor |
| F | CO to $CO_2$ Converter |
| G | Absorber |
| H | Stripper |
| I | Methane Separator |
| J | C2 Splitter |
| K | Vinyl Acetate Reactor |
| L | Vinyl Acetate Refining |

TABLE 1-continued

| Process | Description |
|---------|-------------|
| M | Ethylene Oxide Reactor |
| N | Ethylene Derivatives |

All or a portion of stream 205 may be subjected to a further acetic acid refining process (C), and the resulting substantially purified acetic acid stream (206) may be directly sold (228) and/or conducted into subsequent processes (D) that produce acetic-acid derived chemicals (229). Alternatively or additionally, all or a portion of the resultant acetic acid (207) may be combined with ethylene (222) and oxygen (202C) in a vinyl acetate reactor (K) to produce VAM. The resultant product stream (225) can then be separated in a vinyl acetate refining facility (L) into a stream containing the gaseous reactants (226), which can be fed back into the vinyl acetate reactor, and a stream containing the VAM product (227), which can be sold and/or incorporated into other products, such as ethylene-vinyl acetate copolymers.

The ethylene-containing product stream (204) is compressed to a higher pressure by a compressor (E). The resultant high pressure ethylene-containing stream (208) is then combined with additional oxygen (202B) and subjected to a $CO$-to-$CO_2$ conversion process (F) to remove any carbon monoxide by-product from A by converting it to carbon dioxide. The resultant product stream (209) is then subjected to an absorber (G) and a stripper (H) to remove carbon dioxide (232). The carbon dioxide may be recovered or incorporated into other parts of the process, such as being used as a blowing agent in the formation of ethylene-vinyl acetate foams.

The resultant product stream (210) is then subjected to a methane separation process (I) in which the ethylene and ethane are separated from the light gases, which predominantly comprises methane, as well as minor amounts of unreacted oxygen, carbon monoxide, and other light-boiling gases. The resultant methane-enriched natural gas stream (213) can be then introduced into a natural gas stream (219) for subsequent processing and/or transmission. Alternatively or additionally, all or a portion of 213 (i.e., 214) may also be added to stream 218 to be recycled to the EODH reactor. Alternatively or additionally, all or a portion of 213 (i.e., 215) may be further utilized in integrated processes according to aspects of the present invention, e.g., methane-enriched gas stream 215 may be used as a diluent in an integrated ethylene oxide reaction (M). In many cases, 219 will be sufficiently pure to be considered "pipeline quality" dry natural gas.

The resultant ethylene-containing stream (216) is subjected to a separation process to remove any remaining ethane from the stream in a C2 Splitter (J). The resultant predominantly ethane stream (217) may be recycled to the EODH reactor (218), and the resultant predominantly ethylene stream (220) can be used in a variety of processes. All or a portion of 220 may be sold directly as substantially pure ethylene (i.e., 221). Alternatively or additionally, all or a portion of 220 (i.e., 230) may be subjected to a conversion process (N) that may produce a variety of ethylene derivatives (231). Alternatively or additionally, all or a portion of 220 (i.e., 223) may be combined with oxygen (202D) and subjected to an ethylene oxide reaction (M) to produce an ethylene oxide product stream (224), which may be sold directly or used in subsequent processes for producing ethylene oxide derivatives, e.g., ethylene glycol, and/or other derivatives. Alternatively or additionally, all or a portion of the 220 (i.e., 222) may be combined with oxygen (202C) and acetic acid from the EODH process (207) in a catalytic vinyl acetate reactor (K). The resultant product stream can then be separated in a vinyl acetate separator (L) into stream containing the gaseous reactants (226), which can be fed back into the vinyl acetate reactor, and a stream containing the VAM product (227), which can be sold and/or incorporation into other products, such as ethylene-vinyl acetate copolymers. Alternatively or additionally, all or a portion of 227 may be utilized in a subjected to a conversion process in which VAM is combined with ethylene, e.g., to produce ethylene-vinyl acetate copolymers.

While certain embodiments have been described with a certain degree of particularity, it is manifest that many changes may be made in the details of construction and the arrangement of components without departing from the spirit and scope of this disclosure. It is understood that the invention is not limited to the embodiments set forth herein for purposes of exemplification.

EXAMPLES

The following examples provide one of ordinary skill in the art with additional details about implementing exemplary embodiments of the present invention. These exemplary embodiments are not intended to limit the scope of this disclosure.

Example 1

Figure 3:
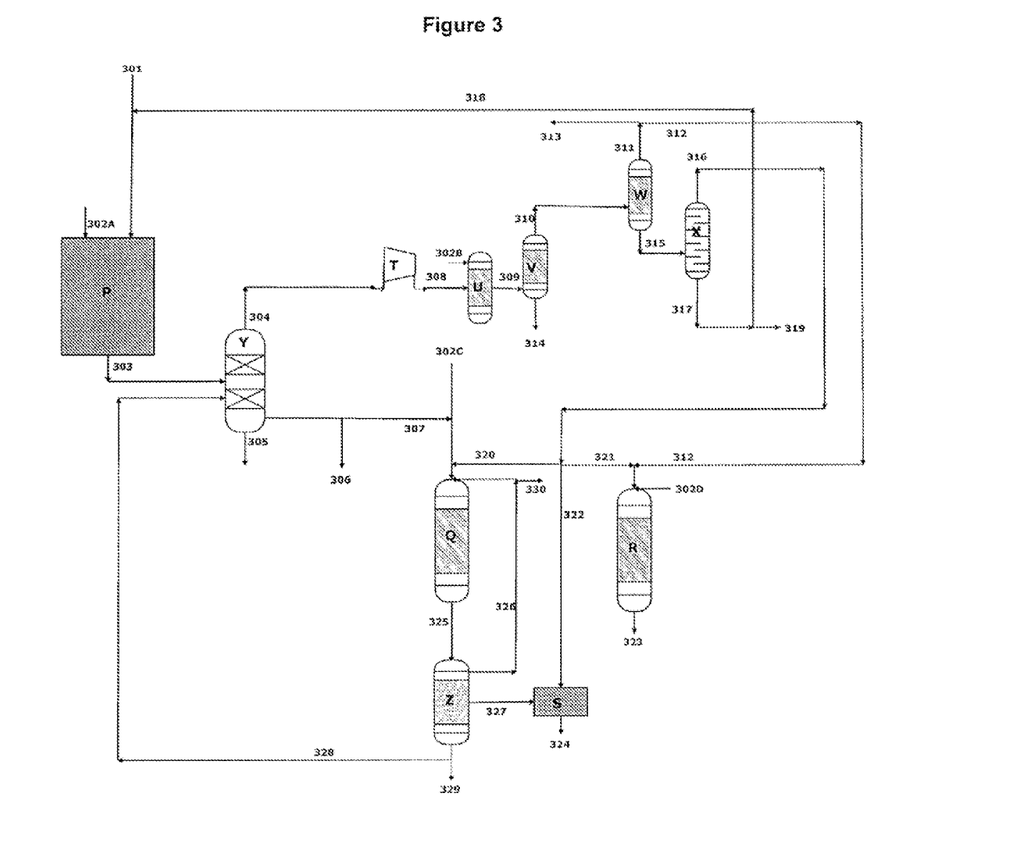
FIG. 3 is a process flow diagram showing an embodiment according to one aspect of the present invention that is set forth in Example 1 in which an ethane-containing natural gas stream provides the feedstock for a process that produces relatively purified, i.e. methane-enriched, natural gas, acetic acid, VAM, EO, and EVAc.

Various models of the embodiments of the present invention were created using ASPEN to simulate the reaction conditions and composition of the product streams. The modeled processes are summarized below in Table 2. The conditions of the modeled process and the relevant compositions of the various reactant and product streams indicated in FIG. 3 are summarized below in Table 3. Overall, the modeled process achieved percent selectivities toward VAM and EO of approximately 94% and 86%, respectively.

TABLE 2

| Process | Description |
|---------|-------------|
| P | EODH Catalytic Reaction System |
| Q | Vinyl Acetate Reaction System |
| R | Ethylene Oxide Reaction System |
| S | Ethylene-Vinyl Acetate Copolymer Reaction System |
| T | Compressor |
| U | CO to $CO_2$ Converter |
| V | $CO_2$ Removal System |
| W | Methane Separator |
| X | C2 Splitter |
| Y | Acetic Acid Separation |
| Z | Vinyl Acetate Refining |

TABLE 3

| | Mole Flow Lbmol/hr | | | | | | | | | | | | |
|---|---|---|---|---|---|---|---|---|---|---|---|---|---|
| | 301 | 302A | 302B | 302C | 302D | 303 | 304 | 305 | 306 | 307 | 308 | 309 | 310 |
| NITROGEN | 0 | 88.2 | 14.7 | 12.10 | 12.74 | 88.2 | 88.2 | 0 | 0 | 0 | 88.2 | 102.9 | 102.9 |
| OXYGEN | 0 | 1710 | 285 | 234.6 | 247 | 118.77 | 118.77 | 0 | 0 | 0 | 118.77 | 0 | 0 |

TABLE 3-continued

| | | | | | | | | | | | | | |
|---|---|---|---|---|---|---|---|---|---|---|---|---|---|
| ARGON | 0 | 1.8 | 0.3 | 0.25 | 0.26 | 1.8 | 1.8 | 0 | 0 | 0 | 1.8 | 2.1 | 2.1 |
| WATER | 0 | 0 | 0 | 0 | 0 | 2122.1 | 129.27 | 2326.9 | 0 | 129.3 | 129.27 | 509.95 | 509.95 |
| CARBON-MONOXIDE | 0 | 0 | 0 | 0 | 0 | 70.10 | 70.10 | 0 | 0 | 0 | 70.10 | 69.75 | 69.75 |
| CARBON-DIOXIDE | 0 | 0 | 0 | 0 | 0 | 224.32 | 224.32 | 0 | 0 | 0 | 224.32 | 437.92 | 4.38 |
| METHANE | 27303 | 0 | 0 | 0 | 0 | 27303 | 27303 | 0 | 0 | 0 | 27303 | 27164.5 | 27164.5 |
| ETHANE | 1965 | 0 | 0 | 0 | 0 | 5187.28 | 5187.28 | 0 | 0 | 0 | 5187.28 | 5160.97 | 5160.97 |
| N-BUTANE | 42 | 0 | 0 | 0 | 0 | 42 | 0 | 42 | 0 | 0 | 0 | 0 | 0 |
| ETHYLENE | 0 | 0 | 0 | 0 | 0 | 1415.92 | 1415.92 | 0 | 0 | 0 | 1415.92 | 1408.73 | 1408.73 |
| PROPANE | 507 | 0 | 0 | 0 | 0 | 507 | 507 | 0 | 0 | 0 | 507 | 504.43 | 504.43 |
| ACETIC-ACID | 0 | 0 | 0 | 0 | 0 | 273.38 | 0 | 0 | 0 | 273.38 | 0 | 0 | 0 |
| ACETAL-DEHYDE | 156 | 0 | 0 | 0 | 0 | 156 | 0 | 156.12 | 0 | 0 | 0 | 0 | 0 |
| VINYL-ACETATE | 0 | 0 | 0 | 0 | 0 | 0 | 0 | 0 | 0 | 0 | 0 | 0 | 0 |
| ETHYLENE-OXIDE | 0 | 0 | 0 | 0 | 0 | 0 | 0 | 0 | 0 | 0 | 0 | 0 | 0 |
| ETHYLENE-VINYL-ACETATE | 0 | 0 | 0 | 0 | 0 | 0 | 0 | 0 | 0 | 0 | 0 | 0 | 0 |
| Total Flow lbmol/hr | 30000 | 1800 | 300 | 247 | 260 | 37536.8 | 35045.7 | 2552.12 | 0 | 402.7 | 35045.7 | 35361.2 | 34927.7 |
| Temperature F. | 86 | 86 | 86 | 86 | 86 | 662 | 72.52 | 72.52 | | 72.5 | 492.2 | 662 | −22 |
| Pressure psia | 300 | 250 | 250 | 250 | 250 | 300 | 50 | 50 | | 50 | 500 | 500 | 436.409 |

| | Mole Flow Lbmol/hr | | | | | | | | |
|---|---|---|---|---|---|---|---|---|---|
| | 311 | 312 | 313 | 314 | 315 | 316 | 317 | 318 | 319 | 320 |
| NITROGEN | 102.9 | 30.87 | 72.03 | 0 | 0 | 0 | 0 | 0 | 0 | 0 |
| OXYGEN | 0 | 0 | 0 | 0 | 0 | 0 | 0 | 0 | 0 | 0 |
| ARGON | 2.1 | 0.63 | 1.47 | 0 | 0 | 0 | 0 | 0 | 0 | 0 |
| WATER | 504.85 | 151.45 | 353.39 | 0 | 5.10 | 0.00 | 5.10 | 5.10 | 0 | 0 |
| CARBON-MONOXIDE | 69.75 | 20.92 | 48.82 | 0 | 0 | 0 | 0 | 0 | 0 | 0 |
| CARBON-DIOXIDE | 4.38 | 1.31 | 3.07 | 433.54 | 0 | 0 | 0 | 0 | 0 | 0 |
| METHANE | 27164.5 | 8149.34 | 19015.1 | 0 | 0 | 0 | 0 | 0 | 0 | 0 |
| ETHANE | 0 | 0 | 0 | 0 | 5160.97 | 0 | 5161 | 5044.8 | 116.12 | 0 |
| N-BUTANE | 0 | 0 | 0 | 0 | 0 | 0 | 0 | 0 | 0 | 0 |
| ETHYLENE | 0 | 0 | 0 | 0 | 1408.73 | 1394.64 | 14.09 | 13.95 | 0.14 | 309.45 |
| PROPANE | 0 | 0 | 0 | 0 | 504.43 | 0 | 504.43 | 0 | 504.43 | 0 |
| ACETIC-ACID | 0 | 0 | 0 | 0 | 0 | 0 | 0 | 0 | 0 | 0 |
| ACETAL-DEHYDE | 0 | 0 | 0 | 0 | 0 | 0 | 0 | 0 | 0 | 0 |
| VINYL-ACETATE | 0 | 0 | 0 | 0 | 0 | 0 | 0 | 0 | 0 | 0 |
| ETHYLENE-OXIDE | 0 | 0 | 0 | 0 | 0 | 0 | 0 | 0 | 0 | 0 |
| ETHYLENE-VINYL-ACETATE | 0 | 0 | 0 | 0 | 0 | 0 | 0 | 0 | 0 | 0 |
| Total Flow lbmol/hr | 27848.4 | 8354.5 | 19493.9 | 433.5 | 7079.2 | 1394.6 | 5684.6 | 5063.9 | 620.7 | 309.5 |
| Temperature F. | −57.9 | 22.18 | 2218.5 | 662 | −57.9 | −57.9 | −57.9 | −57.9 | −57.9 | −57.9 |
| Pressure psia | 200 | 200 | 200 | 500 | 200 | 200 | 200 | 200 | 200 | 200 |

| | | Mole Flow Lbmol/hr | | | | | | | | |
|---|---|---|---|---|---|---|---|---|---|---|
| | | 321 | 322 | 323 | 324 | 325 | 326 | 327 | 328 | 329 | 330 |
| | NITROGEN | 0 | 0 | 43.61 | 0 | 251.06 | 251.06 | 0 | 0 | 0 | 12.60 |
| | OXYGEN | 0 | 0 | 42.01 | 0 | 96.34 | 96.34 | 0 | 0 | 0 | 0 |
| | ARGON | 0 | 0 | 0.89 | 0 | 4.94 | 4.94 | 0 | 0 | 0 | 0.25 |
| | WATER | 0 | 0 | 215.96 | 0 | 463.86 | 0 | 0 | 463.40 | 0.46 | 10.78 |
| | CARBON-MONOXIDE | 0 | 0 | 37.67 | 0 | 17.70 | 17.70 | 0 | 0 | 0 | 1.31 |
| | CARBON-DIOXIDE | 0 | 0 | 49.07 | 0 | 54.68 | 54.68 | 0 | 0 | 0 | 70.81 |
| | METHANE | 0 | 0 | 8149.3 | 0 | 0 | 0 | 0 | 0 | 0 | 0 |
| | ETHANE | 0 | 0 | 0 | 0 | 0 | 0 | 0 | 0 | 0 | 0 |
| | N-BUTANE | 0 | 0 | 0 | 0 | 0 | 0 | 0 | 0 | 0 | 0 |
| | ETHYLENE | 265.46 | 819.73 | 4.96 | 0.00 | 41.75 | 41.75 | 0 | 0 | 0 | 0.01 |
| | PROPANE | 0 | 0 | 0 | 0 | 0 | 0 | 0 | 0 | 0 | 0 |
| | ACETIC-ACID | 0 | 0 | 4.96 | 0 | 0 | 0 | 0 | 0 | 0 | 0 |
| | ACETAL-DEHYDE | 0 | 0 | 0 | 0 | 0.12 | 0 | 0 | 0.12 | 1.2E−04 | 0 |

TABLE 3-continued

| | | | | | | | | | | |
|---|---|---|---|---|---|---|---|---|---|---|
| VINYL-ACETATE | 0 | 0 | 0 | 3.6E−06 | 273.24 | 0 | 273.24 | 0 | 0 | 0 |
| ETHYLENE-OXIDE | 0 | 0 | 223.29 | 0 | 0 | 0 | 0 | 0 | 0 | 0 |
| ETHYLENE-VINYL-ACETATE | 0 | 0 | 0 | 819.73 | 0 | 0 | 0 | 0 | 0 | 0 |
| Total Flow lbmol/hr | 265.5 | 819.7 | 8771.8 | 819.7 | 1203.8 | 466.5 | 273.2 | 463.6 | 0.5 | 95.8 |
| Temperature F. | −57.9 | −57.9003 | 482 | 212 | 356 | 122 | 122 | 122 | 122 | 662 |
| Pressure psia | 200 | 200 | 300 | 5 | 135 | 50 | 50 | 50 | 50 | 500 |

As shown in Table 3, the modeled process may yield a variety of process streams. For example, product stream (327) comprises a substantial quantity of vinyl acetate, product stream (324) comprises a substantial quantity of ethylene-vinyl acetate, and product stream (323) comprises a substantial quantity of ethylene oxide. Alternatively or additionally, all or a portion of the acetic acid produced may be recovered as a product stream (i.e., 306). However, in this example, the acetic acid product stream (307) is directed to vinyl acetate reaction system (Q) and substantially consumed in the production of vinyl acetate stream (325).

Economic modeling suggests the process is advantaged for economies of scale. For example, the capital cost to implement the process for production of EO and VAM can be reduced by up to approximately 75% at smaller scale while remaining cost competitive to world scale facilities producing the same products. Production costs, including capital payback, are about 10% lower for VAM and about 23% lower for EO while consuming all ethylene produced for like scale comparisons.

In another example, one process configuration for producing EVA and VAM according to an aspect of the present invention has an initial capital cost that is approximately 44% lower than a world scale facility producing the same products. Production costs for this process configuration are approximately 11% lower for EVA and approximately 5% lower for VAM than the costs of producing those products at a world scale facility. Furthermore, as compared to traditional steam cracking processes, the required energy input is approximately 80% lower and/or carbon dioxide output is approximately 88% lower for processes that implement the present invention.

Unless otherwise indicated, all numbers expressing quantities of ingredients, reaction conditions, and other properties or parameters used in the specification are to be understood as being modified in all instances by the term "about." Accordingly, unless otherwise indicated, it should be understood that the numerical parameters set forth in the following specification and attached claims are approximations. At the very least, and not as an attempt to limit the application of the doctrine of equivalents to the scope of the claims, numerical parameters should be read in light of the number of reported significant digits and the application of ordinary rounding techniques.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A process for selectively removing propane and ethane from a natural gas stream comprising primarily methane to produce pipeline quality natural gas, the process comprising the steps of:
   (a) selectively removing propane from the natural gas stream, resulting in a natural gas stream with a substantially reduced concentration of propane, and a propane stream;
   (b) selectively removing ethane from the propane depleted natural gas stream by reactive separation performed by contacting the natural gas stream with a catalyst at a temperature of between about 250°-400° C., and pressure of between about 1-40 atm., producing an exothermic reaction within the natural gas stream that selectively converts ethane into a product selected from the group consisting of ethylene, acetic acid, and a combination thereof, wherein water and carbon dioxide are produced as by-products of the exothermic reaction, and wherein methane within the natural gas stream is not converted into the product to produce (i) a resulting natural gas stream having a higher concentration of methane, and a substantially reduced concentration of ethane, and (ii) a product stream comprising ethylene, acetic acid, or a combination thereof; and
   (c) utilizing at least a portion of the product stream in a process selected from the group consisting of refining of ethylene, refining of acetic acid, refining of vinyl acetate, polymerization of ethylene vinyl acetate, and polymerization of polyvinyl acetate, and combinations thereof; and
   (d) transmitting the natural gas stream.

2. The process of claim 1, further comprising the step of removing butanes from the natural gas stream prior to the selective removal of the propane, resulting in a natural gas stream with a substantially reduced concentration of butane, and a butane stream.

3. The process of claim 2, further comprising the step of utilizing at least a portion of the butane stream in a butane reactive conversion process, converting the butanes into a product selected from the group consisting of butenes, butadiene, methacrolein, methacrylic acid, and/or methacrylates.

4. The process of claim 1, further comprising the step of removing pentanes from the natural gas stream by reactive separation, prior to the selective removal of the propane, resulting in a natural gas stream with a substantially reduced concentration of pentane, and a stream comprising pentenes, pentane derivatives, or pentene derivatives.

5. The process of claim 4, wherein in the reactive separation step of removing pentanes from the natural gas stream, other $C_{4+}$ hydrocarbons are reactively separated from the natural gas stream.

6. The process of claim 1, wherein the product stream comprises ethylene and acetic acid, and the process further comprises the step of reacting the ethylene and the acetic acid to produce vinyl acetate monomer.

7. The process of claim 6, wherein the conversion of ethane into ethylene and acetic acid produces ethylene and acetic acid in a ratio so that the ethylene and acetic acid so produced is substantially consumed in the production of vinyl acetate monomer.

8. The process of claim 6, further comprising the step of reacting the vinyl acetate monomer to produce a polymer selected from the group consisting of an ethylene-vinyl acetate copolymer and polyvinyl acetate.

9. The process of claim 8, wherein the polymer is an ethylene vinyl acetate copolymer.

10. The process of claim 1, wherein said catalyst comprises a catalyst that has an ethylene selectivity of at least about fifty percent (50%).

11. The process of claim 1, wherein at least a portion of the byproduct carbon dioxide is utilized in the production of ethylene vinyl acetate copolymers and foams.

12. The process of claim 1, further comprising injecting at least a portion of the by-product carbon dioxide into a natural gas or crude oil well.

13. The process of claim 1, wherein the natural gas stream having a higher concentration of methane is "pipeline quality" dry natural gas.

14. The process of claim 1, wherein carbon monoxide is produced as a by-product and further comprising utilizing at least a portion of the by-product carbon monoxide in a process for producing methanol and other products derived from carbon monoxide.

15. The process of claim 1, wherein said natural gas stream is raw natural gas obtained directly from a well.

16. The process of claim 1, wherein said natural gas stream has been pre-purified to remove non-inert and non-hydrocarbon components from the natural gas stream.

17. The process of claim 1, wherein a portion of the ethylene is selectively removed by at least one process selected from the group consisting of adsorption and metal-complexation.

18. The process of claim 1, wherein the step of contacting the natural gas stream with a catalyst comprises an ethane oxydehydrogenation catalytic process.

19. The process of claim 18, further comprising converting at least a portion of said ethylene to at least one ethylene derivative selected from the group consisting of ethylene oxide, ethylene glycol, polyethylene glycols, glycol ethers, ethylene amine, ethylene diamines, other derivatives of ethylene oxide, an ethylene-containing elastomer, polyethylene, ethylene dichloride, ethanol and other alcohols, acetaldehyde, propionaldehyde, crotonaldehyde and other $C_{4+}$ aldehydes, acids, ethyl benzene, styrene, styrene derivatives, and ethylene dimers.

20. The process of claim 1, further comprising converting at least a portion of said acetic acid to at least one acetic acid derivative selected from the group consisting of acetaldehyde, acetic anhydride, ethanol and other alcohols, crotonoaldehyde and other $C_{4+}$ aldehydes, and acids.

21. The process of claim 1, wherein at least one other component of the natural gas stream is used as a non-reactive diluent in a catalytic oxidation or oxydehydrogenation reaction.

22. The process of claim 21, wherein the at least one other component of the natural gas stream used as a non-reactive diluent is methane.

23. The process of claim 21, wherein at least one product of the catalytic oxidation reaction is selected from the group consisting of ethylene oxide, ethylene glycol, ethanol, propylene oxide, propylene glycol, propanol, polypropylene, vinyl acetate, propylene, acrylates, acrolein, acrylic acid, butenes, butadiene, methacrolein, methacrylic acid, and methacrylates.

24. The process of claim 1, wherein at least one other component of the natural gas stream is used as a non-reactive diluent in an ethane oxydehydrogenation reaction.

25. The process of claim 23, wherein the feed stream to the catalytic oxidation reaction comprises the product stream from an ethylene oxydehydrogenation reaction, from which any acetic acid and other less-volatile components have been removed, but from which the ethylene has not been removed.

26. The process of claim 1, further comprising integrating heat recovery and recapture of the excess heat from the exothermic process to provide a heat source for at least one other integrated process.

27. The process of claim 26, wherein the at least one other integrated process is selected from the group consisting of refining, distillation, gas compression, heating, and electricity co-generation.

28. The process of claim 26, wherein one of the integrated processes is polymerization of vinyl acetate monomer.

29. The process of claim 1, wherein said resulting natural gas stream comprises at least 90 mole percent methane.

* * * * *